US009636100B2

(12) United States Patent
Wyman et al.

(10) Patent No.: US 9,636,100 B2
(45) Date of Patent: May 2, 2017

(54) TISSUE-TO-BONE REATTACHMENT (75) Inventors: Jeffrey Wyman, Naples, FL (US);
Michael Charles Ferragamo, Foster, RI (US); Stephen Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 47 days.

(21) Appl. No.: 13/251,906

(22) Filed: Oct. 3, 2011

(65) Prior Publication Data
US 2013/0085512 A1    Apr. 4, 2013

(51) Int. Cl.
*A61B 17/04* (2006.01)
*A61F 2/08* (2006.01)

(52) U.S. Cl.
CPC .. *A61B 17/0401* (2013.01); *A61B 2017/0403* (2013.01); *A61B 2017/044* (2013.01);
(Continued)

(58) Field of Classification Search
CPC ..... A61B 17/04; A61B 17/0401; A61B 17/68; A61B 2017/0403; A61B 2017/0404; A61B 2017/0406; A61B 2017/0408; A61B 2017/0409; A61B 2017/0411; A61B 2017/0412; A61B 2017/0414; A61B 2017/0416; A61B 2017/042; A61B 2017/0417; A61B 2017/0419; A61B 2017/0422; A61B 2017/0424; A61B 2017/0425; A61B 2017/0427; A61B 2017/0429; A61B 2017/043; A61B 2017/0432; A61B 2017/0433; A61B 2017/0435; A61B 2017/0437;
(Continued)

(56) References Cited

U.S. PATENT DOCUMENTS

| 2004/0138683 A1 | 7/2004 | Shelton et al. |
| 2005/0033363 A1 | 2/2005 | Bojarski et al. |

(Continued)

FOREIGN PATENT DOCUMENTS

| JP | 2005-237966 A | 9/2005 |
| JP | 2011-516795 A | 5/2011 |

(Continued)

OTHER PUBLICATIONS

International Search Report mailed Feb. 22, 2013 in corresponding International Application No. PCT/US2012/000469.
(Continued)

*Primary Examiner* — Jonathan Miles
*Assistant Examiner* — Kendra Obu
(74) *Attorney, Agent, or Firm* — Burns & Levinson LLP; Joseph M. Maraia (57) ABSTRACT

An assembly and method for reattaching tissue to bone from which the tissue had detached including a tissue fixation member will with a narrow cross section and a suture securely attached to the fixation member, the fixation member being configured to secure the detached tissue, a suture anchor fixable in bone at the region of reattachment, the anchor having an eyelet, the anchor including a textured outer surface, the suture having a free end passable through the eyelet to enable the detached tissue to be drawn into engagement with the bone at the region of reattachment.

8 Claims, 4 Drawing Sheets

(52) U.S. Cl.
CPC .......... *A61B 2017/0404* (2013.01); *A61B 2017/0406* (2013.01); *A61B 2017/0409* (2013.01); *A61B 2017/0414* (2013.01); *A61B 2017/0417* (2013.01); *A61B 2017/0453* (2013.01); *A61F 2/0811* (2013.01)

(58) Field of Classification Search
CPC ...... A61B 2017/0438; A61B 2017/044; A61B 2017/0441; A61B 2017/0443; A61B 2017/0445; A61B 2017/046; A61B 2017/0448; A61B 2017/045; A61B 2017/0451; A61B 2017/0453; A61B 2017/0454; A61B 2017/0456; A61B 2017/0458; A61B 2017/0459; A61B 2017/0461; A61B 2017/0462; A61B 2017/0464; A61B 2017/0446; A61F 2/08; A61F 2/0805; A61F 2/0811; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087; A61F 2002/0876; A61F 2002/0882; A61F 2002/0888; A61F 2002/0894

See application file for complete search history.

(56) References Cited

U.S. PATENT DOCUMENTS

| | | | |
|---|---|---|---|
| 2008/0009904 A1* | 1/2008 | Bourque et al. | 606/232 |
| 2008/0033487 A1 | 2/2008 | Schwartz et al. | |
| 2008/0103528 A1* | 5/2008 | Zirps et al. | 606/232 |
| 2009/0054928 A1* | 2/2009 | Denham | A61B 17/0401 606/232 |
| 2009/0082805 A1* | 3/2009 | Kaiser et al. | 606/228 |
| 2009/0157124 A1* | 6/2009 | Ferragamo et al. | 606/301 |
| 2009/0312776 A1 | 12/2009 | Kaiser et al. | |
| 2010/0114162 A1* | 5/2010 | Bojarski | A61B 17/0401 606/228 |
| 2010/0160963 A1* | 6/2010 | Fallin et al. | 606/232 |
| 2010/0256678 A1* | 10/2010 | Ducharme | 606/232 |
| 2010/0318125 A1* | 12/2010 | Gerber et al. | 606/232 |
| 2011/0112576 A1* | 5/2011 | Nguyen et al. | 606/232 |
| 2013/0006302 A1* | 1/2013 | Paulk | A61B 17/0401 606/232 |

FOREIGN PATENT DOCUMENTS

| | | |
|---|---|---|
| JP | 2011-517605 A | 6/2011 |
| WO | 9529637 | 11/1995 |
| WO | 2004037094 | 5/2004 |
| WO | 2009055800 | 4/2009 |
| WO | 2009055800 A1 | 4/2009 |

OTHER PUBLICATIONS

Patent Examination Report from related Australian Application No. 2012321349 issued Jun. 3, 2016.
Second Office Action from related Chinese Application No. 201280059495.4 issued May 26, 2016.
Office Action from related Japanese Application No. 2014-534541 issued Sep. 5, 2016.
Third Office Action from related Chinese Application No. 201280059495.4 issued Aug. 24, 2016.
Office Action from related Russian Application No. 201414628/14(022908) issued Sep. 6, 2016.
Office Action from related Russian Application No. 201414628/14(022908) issued Dec. 22, 2016.
Office Action from related Chinese Application No. 201280059495.4 issued Dec. 29, 2016.

* cited by examiner

TISSUE-TO-BONE REATTACHMENT

BACKGROUND OF INVENTION

Meniscus repairs have been shown to be effective, especially with tears in the peripheral one-third of the meniscus. Various techniques have evolved to perform this demanding procedure. Initially, open repairs were done that proved the feasibility of the procedure. Subsequently, several techniques involving the arthroscope were developed to assist in these repairs. Most of the techniques have been a variation of the outside-in, or more commonly, the inside-out techniques. These repair procedures have shown to be technically demanding, but more importantly, have inherent risks to the neurovascular structures about the knee. Most of the techniques describe an ancillary incision, either medial and/or lateral, for the purpose of performing the repair and specifically to protect these important structures. In addition, these repairs tether the posterior capsule, causing extension difficulties in the post-operative rehabilitation phase.

Accordingly, there exists a need for an assembly for meniscal repair that reduces the difficulties and time to repair the meniscus.

SUMMARY OF INVENTION

According to one aspect of the present invention, there is provided an assembly for meniscal repair including a first tissue fixation member configured to secure a meniscal tissue, a suture anchor having a proximal end, a distal end, a central axis defined therethrough, an eyelet, and a textured outer surface, and a first suture configured to be coupled to the first tissue fixation member and configured to be received through the eyelet of the suture anchor.

According to another aspect of the present invention, there is provided a method for meniscal repair including providing a first tissue fixation member configured to secure a meniscal tissue, a suture anchor having an eyelet, and a first suture, securing the first suture to the first tissue fixation member, securing the first tissue fixation member to a meniscal tissue, threading the first suture through the eyelet of the suture anchor, securing the suture anchor within a bone, and tensioning the first suture within the suture anchor.

According to another aspect of the present invention, there is provided a kit for meniscal repair including at least one tissue fixation member configured to secure a meniscal tissue, a suture anchor comprising an eyelet, at least one suture configured to be coupled to the at least one tissue fixation member and configured to be received through the eyelet of the suture anchor, and a delivery device configured to assist with delivery of the at least one tissue fixation member into a body.

DETAILED DESCRIPTION

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art will appreciate, different persons may refer to the same feature or component by different names. This document does not intend to distinguish between components or features that differ in name but not function. The figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component is coupled to a second component, that connection may be through a direct connection, or through an indirect connection via other components, devices, and connections. Further, the terms "axial" and "axially" generally mean along or substantially parallel to a central or longitudinal axis, while the terms "radial" and "radially" generally mean perpendicular to a central, longitudinal axis.

Figure 1A:
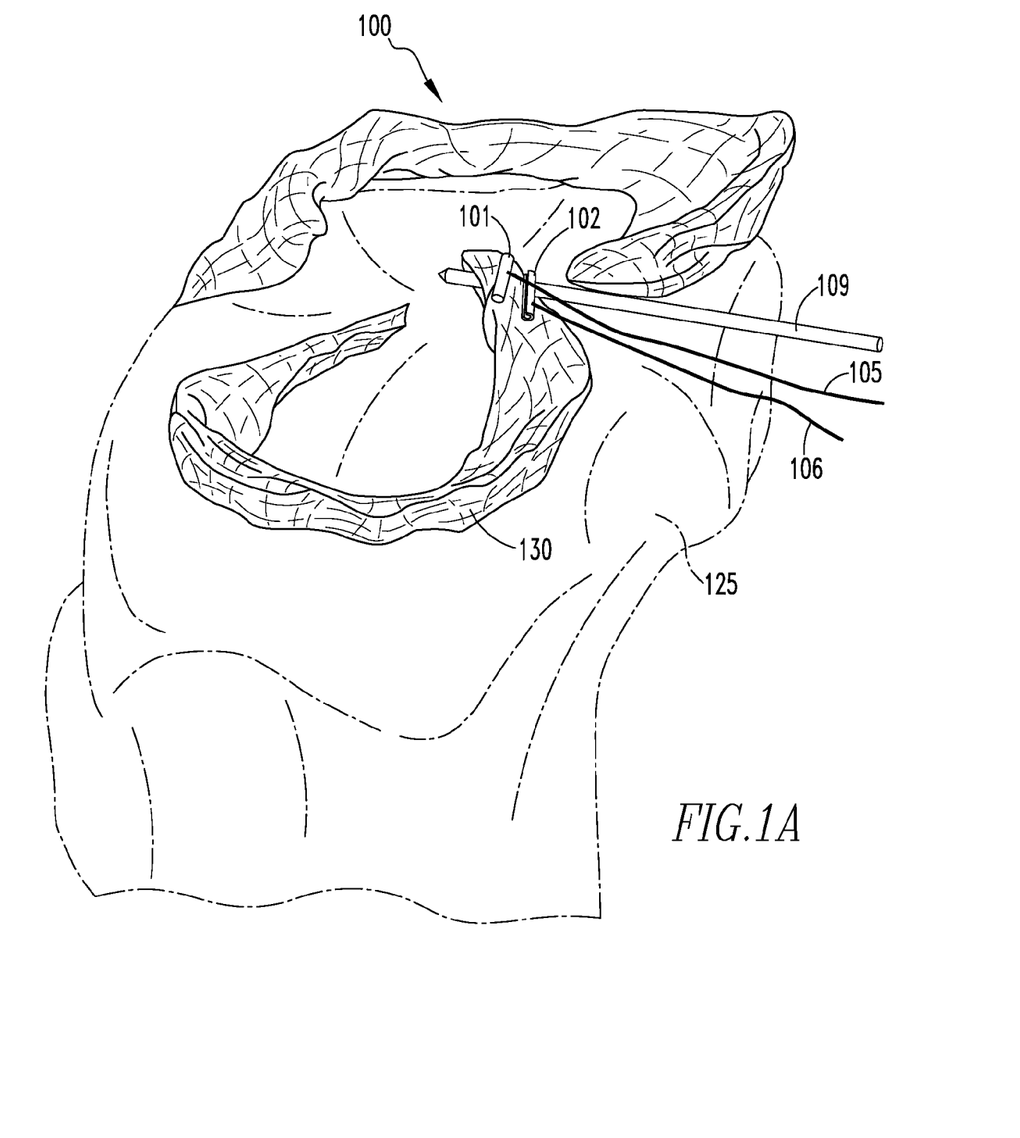
FIGS. 1A-1C are multiple views of an assembly for meniscal repair in accordance with embodiments disclosed herein.
Figure 1B:
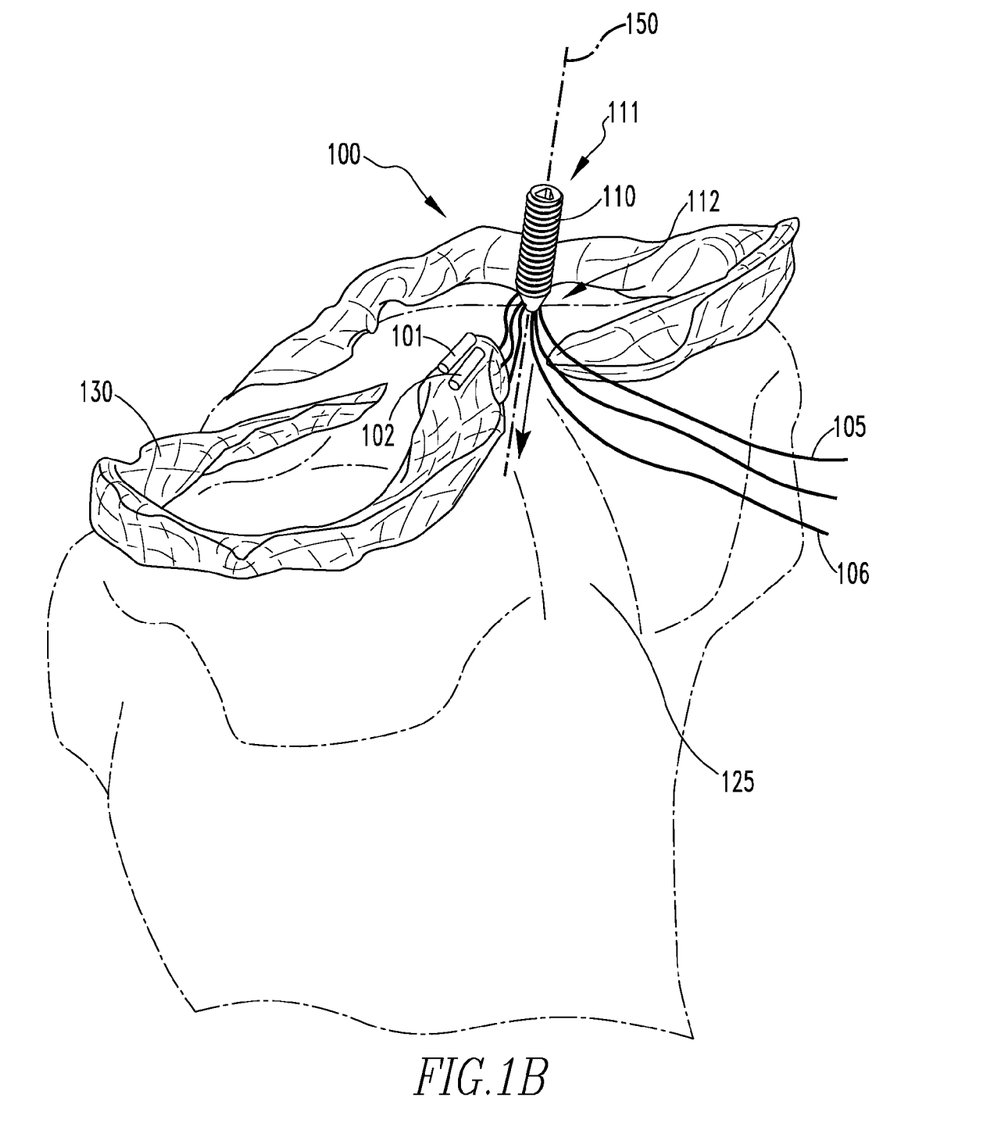
Figure 1C:
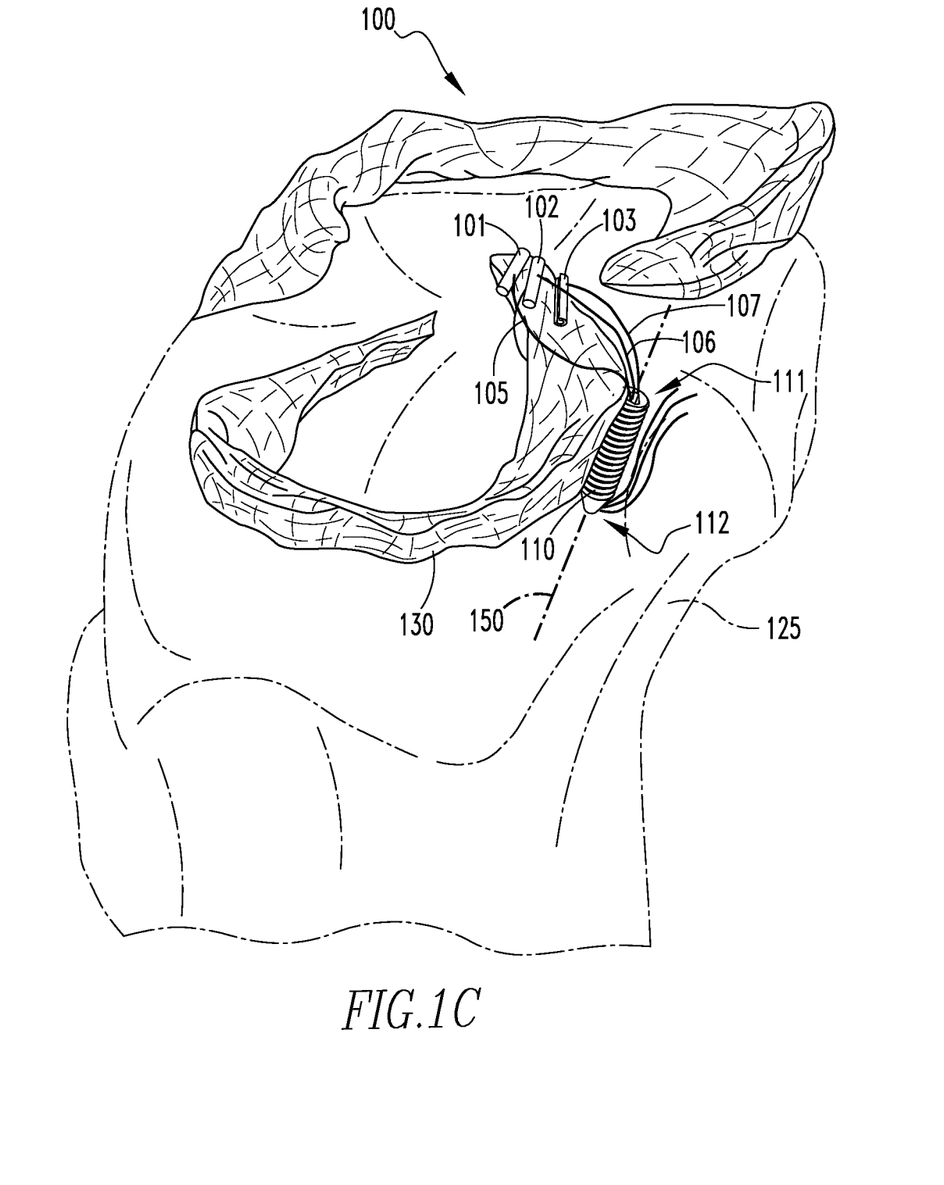

Referring generally to FIGS. 1A-1C, an assembly for meniscal repair 100, according to embodiments disclosed herein, is shown. In one or more embodiments, the assembly 100 may include a first tissue fixation member 101 configured to secure a meniscal tissue 130, a suture anchor 110 having a proximal end 111, a distal end 112, a central axis 150 defined therethrough, an eyelet (not shown), and a textured outer surface, and a first suture 105 configured to be coupled to the first tissue fixation member 101 and configured to be received through the eyelet of the suture anchor 110.

In one or more embodiments, the first tissue fixation member 101 may be a substantially rigid, bar or rod-shaped member. Alternatively, in one or more embodiments, the first tissue fixation member 101 may have a curved shape and may be formed from a flexible material, such as a plastic or polymer. In one or more embodiments, the first tissue fixation member 101 may be formed from any biocompatible material known in the art, including plastics, polymers, metals, and any combination thereof. The first tissue fixation member 101 may engage with the meniscal tissue 130 and may be used to secure the meniscal tissue 130, e.g., against a tibia 125.

In one or more embodiments, the assembly 100 may also include a second tissue fixation member 102 configured to secure the meniscal tissue 130. In one or more embodiments, the second tissue fixation member 102 may be substantially identical to the first tissue fixation member 101. For example, as discussed above, in one or more embodiments, the second tissue fixation member 102 may be a substantially rigid, bar or rod-shaped member. Alternatively, in one or more embodiments, the second tissue fixation member 102 may have a curved shape and may be formed from a flexible material, such as a plastic or polymer. In one or more embodiments, the second tissue fixation member 102 may be formed from any biocompatible material known in the art, including plastics, polymers, metals, and any combination thereof. The second tissue fixation member 102, like the first tissue fixation member 101, may engage with the meniscal tissue 130 and may be used to secure the meniscal tissue 130, e.g., against a tibia 125. Those having ordinary skill in the art will appreciate that more than two tissue fixation members may be used in the assembly 100 to assist with securing the meniscal tissue 130. For example, three, four, five, or more tissue fixation members, that may be substantially identical to the first tissue fixation member 101 and the second tissue fixation member 102, may be used in the assembly 100 to assist with securing the meniscal tissue 130.

As shown in FIG. 1A, the first suture 105 is coupled to the first tissue fixation member 101. Further, as shown, a second suture 106 is coupled to the second tissue fixation member 102. In one or more embodiments, each of the first tissue fixation member 101 and the second tissue fixation member 102 may include holes, or notches, formed therethrough, through which each of the first suture 105 and the second suture 106 may be engaged with, or coupled to, the first tissue fixation member 101 and the second tissue fixation member 102, respectively. Those having ordinary skill in the art will appreciate that the first suture 101 and the second suture 102 may be formed from any material known in the art. For example, in one or more embodiments, each of the first suture 101 and the second suture 102 may be formed from a biocompatible polyester or polyester closure tape and may be, for example, a single or double-arm 2-0 braided non-absorbable polyester suture.

As shown in FIGS. 1B and 1C, the suture anchor 110 includes an eyelet (not shown), in which each of the first suture 105 and the second suture 106 are configured to be received through the eyelet of the suture anchor 110. In one or more embodiments, the eyelet of the suture anchor 110 may be a transverse hole that is located between the proximal end 111 and the distal end 112 of the suture anchor 110, and may be formed through the suture anchor 110. Further, as shown, the eyelet may be located near the distal end 112 of the suture anchor 110. However, those having ordinary skill in the art will appreciate that the eyelet may be located at any other position on the suture anchor 110, and that the eyelet is not limited to being formed near the distal end 112 of the suture anchor 110. For example, the eyelet may be formed near the proximal end 111 of the suture anchor 110 or through a region of the suture anchor 110 between the proximal end 111 and the distal end 112 of the suture anchor 110. Those having ordinary skill in the art will appreciate that more than one suture anchor 110 may be included in the assembly 100. For example, two, three, or more suture anchors that may be substantially identical to the suture anchor 110 may be included in the assembly 100.

In one or more embodiments, the textured outer surface of the suture anchor 110 may be formed near the distal end 112 of the suture anchor 110. However, those having ordinary skill in the art will appreciate that the textured outer surface of the suture anchor 110 may be formed any other surface of the suture anchor 110 and that the textured outer surface of the suture anchor 110 is not limited to being formed near the distal end 112 of the suture anchor 110. For example, in one or more embodiments, the textured outer surface of the suture anchor 110 may be formed on the entire outer surface of the suture anchor 110. Alternatively, in one or more embodiments, the textured outer surface of the suture anchor 110 may be formed near the proximal end 111 of the suture anchor.

Further, in one or more embodiments, the textured outer surface of the suture anchor 110 may be a threaded outer surface. In one or more embodiments, the textured outer surface of the suture anchor 110 may be a threaded outer surface that may be configured to self-tap into a bone, e.g., the tibia 125. For example, as will be discussed below, a hole may be formed into the tibia 125. Subsequently, in one or more embodiments, the suture anchor 110 may be aligned with the hole secured within the tibia 125, such that the threaded outer surface of the suture anchor 110 may engage with, and may form corresponding threads within, the hole formed in the tibia 125.

Furthermore, in one or more embodiments, the textured outer surface of the suture anchor 110 may be a stepped outer surface. For example, in one or more embodiments, the outer surface of the suture anchor 110 may include steps, or barbs, that may be configured to reduce the possibility of unwanted removal of the suture anchor 110 from a bone, e.g., the tibia 125. Those having ordinary skill in the art will appreciate that the suture anchor 110 may include any number of steps, or barbs, formed on the outer surface of the suture anchor 110.

In one or more embodiments, the assembly 100 may also include a fixation plug (not shown) that may be configured to engage with the suture anchor 110. For example, in one or more embodiments, the suture anchor 110 may include a longitudinal hole formed along the central axis 150 of the suture anchor 110 to receive the fixation plug. In one or more embodiments, the fixation plug may be configured to secure at least one suture, e.g. the first suture 105 and the second suture 106, within the eyelet of the suture anchor 110. In one or more embodiments, the longitudinal hole formed through the suture anchor 110 along the central axis 150 of the suture anchor 110 may be a threaded hole. For example, in one or more embodiments, the fixation plug may include corresponding threads that may allow the fixation plug to threadably engage with the suture anchor 110, i.e., with the longitudinal hole of the suture anchor 110. As such, in one or more embodiments, the first suture 105 and the second suture 106 may be disposed, or threaded, through the eyelet of the suture anchor 110. Subsequently, in one or more embodiments, the fixation plug may be engaged within the longitudinal hole of the suture anchor 110, which may secure the first suture 105 and the second suture 106 within the eyelet of the suture anchor 110. Those having ordinary skill in the art will appreciate that more than two sutures may be disposed, or threaded, through the eyelet of the suture anchor 110. For example, three, four, five, or more sutures may be threaded through the eyelet of the suture anchor 110, and the fixation plug may be engaged within the longitudinal hole of the suture anchor 110, which may secure any suture disposed through the eyelet of the suture anchor 110 within the suture anchor 110. Further, those having ordinary skill in the art will appreciate that the fixation plug may not necessarily need to have a threaded outer surface in order to engage with the suture anchor 110. For example, in one or more embodiments, an outer diameter of the fixation plug may be substantially equal to, or slightly larger than, the diameter of the longitudinal hole formed in the suture anchor 110. As such, in one or more embodiments, the fixation plug may be secured within, or engaged with, the suture anchor 110, i.e., with the longitudinal hole of the suture anchor 110, by disposing the fixation plug within the longitudinal hole of the suture anchor 110. In one or more embodiments, frictional forces between the fixation plug and an inner surface of the longitudinal hole of the suture anchor 110 may engage with fixation plug within the longitudinal hole of the suture anchor 110 such that any sutures, e.g. the first suture 105 and the second suture 106, that may be disposed through the eyelet may be secured within the suture anchor 110. However, those having ordinary skill in the art will appreciate that a fixation plug may not be necessary in order to secure at least one suture within an eyelet of the suture anchor 110. For example, in one or more embodiments, the eyelet may be formed near the distal end 112 of the suture anchor 110, and the suture anchor 110 may be secured within a bone, e.g., the tibia 125. As such, because the distal end 112 of the suture anchor 110 may be disposed within, and engaged with, the tibia 125, the engagement between the outer surface of the suture anchor 110 and the hole formed in the tibia 125, in which the suture anchor 110 is disposed, may secure at least one suture, e.g., the first suture 105 and the second suture 106, within the eyelet of the suture anchor 110.

Examples and further description of suture anchors and fixation plugs may be disclosed in co-pending U.S. application Ser. No. 12/259,106, titled "Anchor Assembly" and assigned to the assignee of the present disclosure, and hereby incorporated by reference in its entirety.

Figure 2:
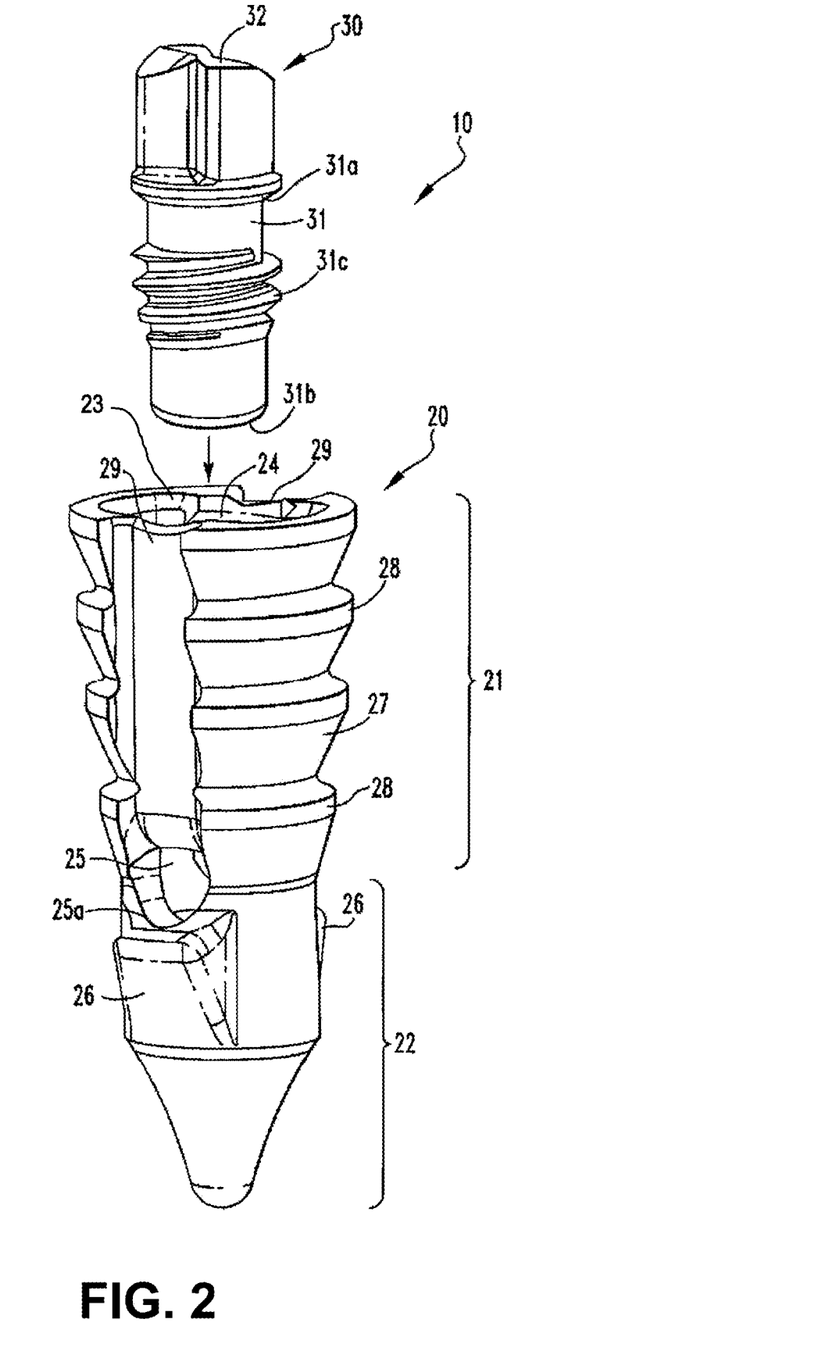
FIG. 2 is an illustration of a suture anchor and associated plug.

FIG. 2 shows one example of an anchor assembly 10. The assembly 10 includes the anchor 20 and the insertion member 30. The anchor 20 includes a proximal portion 21, a distal portion 22, and an inner cavity 23. An opening 24 to the cavity 23 is located at the proximal portion 21 of the anchor 20. A transverse through hole 25 is located between the proximal and distal portions 21,22 and extends through the anchor 20. Openings 25a,b are located at each end of the through hole 25 Located below each opening 25a,b is a protrusion 26. The protrusions 26 facilitate loading of a flexible member, such as a suture, through the through hole 25, and allow for the creation of a path in the wall of a bone hole when the anchor 20 is inserted into bone hole. The outer surface 27 of the proximal portion 21 also includes barbs 28 for substantially reducing the possibility of removal of the anchor 20 when inserted into bone. The outer surface 27 also includes slots 29 extending from the openings 25a,b of the through hole 25 to the proximal portion 21 of the anchor 20. The slots 29 intersect the barbs 28 and are configured for housing of the suture after positioning of the anchor 20 in bone. The cavity 23 extends into the through hole 25 and includes a proximal portion 23a and a threaded distal portion 23b for receipt of a fixation plug 30.

The fixation plug 30 includes a body 31, having a proximal end portion 31a and a flat distal end portion 31b, and a head 32 coupled to the proximal end portion 31a. The head 32 is configured for engagement with a delivery tool and the body 31 includes threads 31c that are configured for engagement with the threads 23c of the cavity 23 when the insertion member is arranged within the cavity 23.

A method for meniscal repair, according to embodiments disclosed herein, may include providing a first tissue fixation member configured to secure a meniscal tissue, a suture anchor having an eyelet, and a first suture, securing the first suture to the first tissue fixation member. The method may also include making a single incision into a skin and forming a portal into a body and forming a hole within the bone, and engaging the first tissue fixation member and a delivery device and disposing the delivery device and the first tissue fixation member through the portal, into the body. Further, in one or more aspects, the method may also include engaging the second tissue fixation member and the delivery device and disposing the delivery device and the second tissue fixation member through the portal, into the body.

For example, referring to FIG. 1A, the first tissue fixation member 101 and the second tissue fixation member 102 are configured to secure the meniscal tissue 130. As shown, each of the first tissue fixation member 101 and the second tissue fixation member 102 were delivered through the meniscal tissue 130 with a delivery device 109. In one or more embodiments, each of the first tissue fixation member 101 and the second tissue fixation member 102 may be secured to, or engaged with, the delivery device 109. In one or more embodiments, the delivery device 109 may include a cannulated spinal needle and an obturator (not shown), e.g., a deployment rod (not shown). Further, in one or more embodiments, the delivery device 109 may be formed from any substantially rigid or from a flexible, biocompatible material known in the art. For example, the cannulated spinal needle of the delivery device 109 may be formed from biocompatible plastics, polymers, metals, and any combination thereof. In one or more embodiments, the cannulated spinal needle may be a 17 gauge spinal needle. However, those having ordinary skill in the art will appreciate that the cannulated spinal needle may not necessarily need to be a 17 gauge spinal needle.

Still referring to FIG. 1A, as discussed above, each of the first tissue fixation member 101 and the second tissue fixation member 102 may include holes, or notches, formed therethrough, through which each of the first suture 105 and the second suture 106 may be engaged with, or coupled to, the first tissue fixation member 101 and the second tissue fixation member 102, respectively. As such, according to one or more aspects, once the first suture 105 and the second suture 106 have been coupled to the first tissue fixation member 101 and the second tissue fixation member 102, respectively, each of the first tissue fixation member 101 and the second tissue fixation member 102 may be disposed within the delivery device 109, e.g., within the cannulated spinal needle (not shown).

Once a single incision into a skin, forming a portal (not shown) into a body, each of the first tissue fixation member 101 and the second tissue fixation member 102 may be disposed through the portal into the body with the delivery device 109. According to one or more aspects, each of the first tissue fixation member 101 and the second tissue fixation member 102 may be engaged with, or secured to, the delivery device by disposing each of the first tissue fixation member 101 and the second tissue fixation member 102 within the delivery device. In one or more embodiments, an inner diameter of the cannulated spinal needle may be slightly larger than a diameter of the tissue fixation members 101, 102. As such, according to one or more aspects, each of the first tissue fixation member 101 and the second tissue fixation member 102 may be disposed within, and received by, the cannulated spinal needle of the delivery device 109. Further, a distal end of the cannulated spinal needle may be angled, such that the distal end of the cannulated spinal needle is configured to pierce the meniscal tissue 130.

According to one or more aspects, the cannulated spinal needle of the delivery device 109 may be inserted through the portal, into the body, and may pierce through the meniscal tissue 130. Once the cannulated spinal needle of the delivery device 109 has pierced the meniscal tissue 130, the obturator may be disposed within the cannula of the cannulated spinal needle from a distal end of the cannulated spinal needle, and may force, or push, at least one of the first tissue fixation member 101 and the second tissue fixation member 102 out of the cannulated spinal needle, i.e., deploy at least one of the first tissue fixation member 101 and the second tissue fixation member 102 from the delivery device 109. Upon deployment of at least one of the first tissue fixation member 101 and the second tissue fixation member 102, the first tissue fixation member 101 and the second tissue fixation member 102 may be reoriented such that a longitudinal axis of the first tissue fixation member 101 and the second tissue fixation member 102 may be substantially parallel to a contacting surface of the meniscal tissue 130. In other words, upon deployment of the first tissue fixation member 101 and the second tissue fixation member 102 from the delivery device 109, the first tissue fixation member 101 and the second tissue fixation member 102 may be reoriented to prevent the first tissue fixation member 101 and the second tissue fixation member 102 from being displaced through the hole formed in the meniscal tissue 130 from the piercing of the cannulated spinal needle of the delivery device through the meniscal tissue 130.

The method may also include securing the first tissue fixation member to a meniscal tissue, threading the first suture through the eyelet of the suture anchor, securing the suture anchor within a bone, and tensioning the first suture within the suture anchor. The method may also include securing a second suture to a second tissue fixation member, threading the second suture through the eyelet of the suture anchor, and tensioning the second suture within the suture anchor.

For example, referring to FIG. 1B, each of the first tissue fixation member 101 and the second tissue fixation member 102 are secured to, or are engaged with, the meniscal tissue 130. Further, as shown in FIG. 1B, each of the first suture 105 and the second suture 106, which are coupled to the first tissue fixation member 101 and the second tissue fixation member 102, respectively, may be threaded, or disposed, through the eyelet (not shown) of the suture anchor 110.

As shown in FIG. 1C, the suture anchor 110 may be secured within the bone, e.g., within the tibia 125. Further, each of the first suture 105 and the second suture 106 may be tensioned within the suture anchor 110 such that the area of the meniscal tissue 130 that is in contact with each of the first tissue fixation member 101 and the second tissue fixation member 102 may be pulled toward the suture anchor 110, i.e., toward the tibia 125. As discussed above, once each of the first suture 105 and the second suture 106 are tensioned, a fixation plug (not shown) may be engaged with the suture anchor to secure any sutures disposed through the eyelet of the suture anchor 110 within the suture anchor 110. Furthermore, as discussed above, in one or more embodiments, three, four, five, or more tissue fixation members, that may be substantially identical to the first tissue fixation member 101 and the second tissue fixation member 102, may be used in the assembly 100 to assist with securing the meniscal tissue 130. For example, as shown in FIG. 1C, a third tissue fixation member 103 may be used in the assembly 100 to assist with securing the meniscal tissue 130 to the tibia 125. As shown, the third tissue fixation member 103 is coupled to a third suture 107, which is also disposed through the eyelet of the suture anchor 110 and is secured within the suture anchor 110.

The method may also include disengaging the first tissue fixation member from the delivery device and removing the delivery device from the body, and disengaging the second tissue fixation member from the delivery device and removing the delivery device from the body. For example, once all of the fixation members, e.g., the first tissue fixation member 101, the second tissue fixation member 102, and the third fixation member 103, are deployed from the delivery device 109, the delivery device 109 may be removed from the body, through the portal described above.

According to one or more aspects, the methods described herein may also be used for other surgical procedures pertaining to the meniscus. For example, according to one or more aspects, the methods described herein may be used to secure, specifically, the anterior horn of a meniscus tear. Further, according to one or more aspects, the methods described herein may be used for a meniscal transplant procedure.

A kit for meniscal repair, according to embodiments disclosed herein, may include at least one tissue fixation member configured to secure a meniscal tissue, a suture anchor comprising an eyelet, at least one suture configured to be coupled to the at least one tissue fixation member and configured to be received through the eyelet of the suture anchor, and a delivery device configured to assist with delivery of the at least one tissue fixation member into a body.

For example, in one or more embodiments, the kit for meniscal repair may include at least one of the first tissue fixation member 101, the second tissue fixation member 102, and the third tissue fixation member 103, the suture anchor 110, and at least one suture configured to be coupled to the at least one tissue fixation member and configured to be received through the eyelet of the suture anchor, e.g., sutures 105, 106, 107. Further, in one or more embodiments, the kit for meniscal repair may include the delivery device 109 configured to assist with delivery of the at least one tissue fixation member into a body. As discussed above, the delivery device 109 may include a cannulated spinal needle and an obturator (not shown), e.g., a deployment rod (not shown), configured to assist with deployment of the tissue fixation members.

Advantageously, embodiments disclosed herein may provide an assembly for meniscal repair that reduces the difficulties and time to repair the meniscus. The aspects of the invention, discussed above, may allow endoscopic meniscal repair to virtually any area of the meniscus and may minimize the danger to neurovascular structures and the need for additional ancillary incisions.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A method of repairing a torn meniscus in a human knee joint by securing a torn portion of the meniscus to a corresponding tibia, the method comprising:
   providing a first tissue fixation member having a narrow cross section, a first suture having a leading end attached to the tissue fixation member and a trailing end, and an anchor having a distal end that narrows to a tip, a proximal end, an inner cavity, a central axis running from the proximal end to the distal end, an opening to the inner cavity positioned at the proximal end, a pair of opposed eyelets, defined in a portion of the distal end of the anchor, into the inner cavity and a pair of opposed slots running along an outer surface of the anchor from a respective eyelet to the opening to the inner cavity at the proximal end;
   passing the first tissue fixation member through a first hole formed in the torn portion of the meniscus, from a first side of the meniscus and out a second side of the meniscus, leaving the first suture trailing end extending from the meniscus first side, and reorienting the tissue fixation member after passing through the torn portion of the meniscus so that the tissue fixation member securely engages with the second side of the torn portion of the meniscus to prevent the tissue fixation member from being drawn back through the first hole formed in the torn portion of the meniscus;

threading the trailing end of the first suture through one eyelet of the anchor and out the other eyelet so as to be adjustably received therein;

placing the tip of the anchor within the tibia at a region of the tibia where the torn portion of the meniscus is to be secured such that the trailing end of the first suture is freely movable within an area defined by the slots between the anchor and the tibia;

urging the torn portion of the meniscus toward and into engagement with the tibia by increasing or decreasing tension on the first suture by drawing or releasing, respectively, the trailing end of the first suture through the eyelets; and with the first suture under tension, securing the first suture to the anchor by tightening an insertion plug housed within the inner cavity until the first suture is secured by the plug to the anchor, wherein urging the torn portion of the meniscus toward and into engagement with the tibia comprises:
positioning the torn portion of the meniscus between the first tissue fixation member and the tibia.

2. The method of claim 1, further comprising making an incision through skin to create a portal into a body.

3. The method of claim 2, further comprising:
engaging the tissue fixation member and a delivery device; and
disposing the delivery device and the tissue fixation member through the portal, into the body.

4. The method of claim 3, further comprising disengaging the first tissue fixation member from the delivery device and removing the delivery device from the body.

5. The method of claim 1, further comprising forming a hole within the tibia.

6. The method of claim 1, further comprising:
providing a second tissue fixation member having a narrow cross section and an attached second suture having a leading end and a trailing end, the leading end being attached to the second tissue fixation member;

passing the second tissue fixation member through a second hole formed in the torn portion of the meniscus, from a third side of the meniscus and out a fourth side of the meniscus, leaving the second suture trailing end extending from the meniscus third side, and reorienting the second tissue fixation member after passing through the torn portion of the meniscus to securely engage the fourth side of the torn portion of the meniscus to prevent the second tissue fixation member from being drawn back through the second hole formed in the torn portion of the meniscus;

threading the trailing end of the second suture through one eyelet and out the other eyelet of the anchor so as to be adjustably received therein;

urging the torn portion of the meniscus toward and into engagement with the tibia by increasing or decreasing tension on the second suture by drawing or releasing, respectively, the trailing end of the second suture through the eyelets; and with each of the first and second sutures under tension, securing the first and second sutures to the anchor by tightening the plug.

7. The method of claim 6, further comprising engaging the second tissue fixation member and a delivery device and disposing the delivery device and the second tissue fixation member through a portal, into the body.

8. The method of claim 7, further comprising disengaging the second tissue fixation member from the delivery device and removing the delivery device from the body.

* * * * *